US012571679B2

(12) United States Patent
Duckett, III

(10) Patent No.: US 12,571,679 B2
(45) Date of Patent: Mar. 10, 2026

(54) IMAGING SPECTROMETER AND CAMERA WITH HIGH SPECTRAL RANGE

(71) Applicant: KARL STORZ Imaging, Inc., Goleta, CA (US)

(72) Inventor: George E. Duckett, III, Castaic, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 257 days.

(21) Appl. No.: 18/401,346

(22) Filed: Dec. 30, 2023

(65) Prior Publication Data

US 2025/0216260 A1      Jul. 3, 2025

(51) Int. Cl.
*G01J 3/28*          (2006.01)
*A61B 5/00*          (2006.01)
(Continued)

(52) U.S. Cl.
CPC .......... *G01J 3/2823* (2013.01); *A61B 5/0075* (2013.01); *A61B 5/0084* (2013.01); *G01J 3/14* (2013.01);
(Continued)

(58) Field of Classification Search
CPC .. G01N 21/93; G01N 21/276; G01N 21/8851; G01N 2021/8887; G01N 2021/936; G06T 7/00
See application file for complete search history.

(56) References Cited

U.S. PATENT DOCUMENTS

2020/0363323  A1*  11/2020  Quaranta ............... G01J 3/0208
2021/0072163  A1*   3/2021  Simkhovich ......... G01N 21/211
(Continued)

OTHER PUBLICATIONS

Rodriquez, K., International Search Report and Opinion, Jan. 22, 2025, pp. 1-9, US International Search Authority, USA.

*Primary Examiner* — Dominic J Bologna
(74) *Attorney, Agent, or Firm* — David N. Villalpando; Jacqueline Cohen

(57)          ABSTRACT

An imaging spectrometer and camera are disclosed including a prism that refracts incident light a spectral range for spectrographic analysis with a shortest wavelength ($\lambda_S$) and a longest wavelength ($\lambda_L$). A diffraction grating is aligned with the prism and diffracts the incident light. The refraction and diffraction for a set of diffraction orders used for the spectrographic analysis both increase a deflection angle of the incident light from an original optical axis. The spectral range spans greater than an octave such that $\lambda_L > 2\lambda_S$. The refraction and diffraction are such that a second diffracted order of $\lambda_S$ does not overlap with a first diffracted order of wavelengths shorter than $\lambda_L$. The second order diffraction for wavelengths between $\lambda_S$ and $\lambda_C$, and the first order diffraction for wavelengths between $\lambda_C$ and $\lambda_L$, are detected in different spatial regions to perform the spectrographic analysis from $\lambda_S$ to $\lambda_L$.

20 Claims, 8 Drawing Sheets

(51) Int. Cl.
G01J 3/12 (2006.01)
G01J 3/14 (2006.01)
G01J 3/18 (2006.01)

(52) U.S. Cl.
CPC ......... *G01J 3/18* (2013.01); *A61B 2562/0233* (2013.01); *G01J 2003/1208* (2013.01); *G01J 2003/2826* (2013.01)

(56) References Cited

U.S. PATENT DOCUMENTS

| | | | |
|---|---|---|---|
| 2022/0229213 A1* | 7/2022 | Zhuang ................ | G02B 5/1842 |
| 2023/0190374 A1 | 6/2023 | Shelton et al. | |
| 2023/0314795 A1* | 10/2023 | Bao ........................... | G01J 3/14 |
| | | | 356/328 |
| 2024/0133824 A1* | 4/2024 | Urano ................... | G01N 21/93 |

\* cited by examiner

100

IMAGING SPECTROMETER AND CAMERA WITH HIGH SPECTRAL RANGE

TECHNICAL FIELD

This disclosure relates to multispectral imaging (MSI) or hyperspectral imaging (HSI) systems, and more particularly to imaging systems and devices including imaging spectrometers and particularly those that can operate over an extended spectral range.

BACKGROUND

Classical video endoscopes are used for color video imaging of an examination area inside the body. Multispectral or hyperspectral imaging can provide users of endoscopes with additional information that can be used during operations or diagnostics. For example, in medical technology, physiological imaging with multispectral or hyperspectral methods may be used to analyze physiological parameters such as hemoglobin content and the oxygenation of hemoglobin in the examination area, which are displayed spatially resolved by false colors. Multispectral and hyperspectral imaging also have a variety of further applications both in and outside the medical field.

To integrate multispectral or hyperspectral imaging capability with a medical scope typically requires an imaging spectrometer construction that is small in size and, depending on the application, inexpensive as compared to typical imaging spectrometers for other applications. To help meet these requirements, a simple spectrometer can be constructed based on a diffraction grating. However, such designs are typically limited to a single octave of spectral range so that the second diffracted orders of the shorter wavelengths are not imaged on top of the first diffracted order of the longer wavelengths.

A common conventional approach to this problem is place a spectral filter near the image plane to filter the second order diffraction from the shortest wavelengths. This approach, however, often leads to a gap in the acquired spectrum due to the physical dimensions of the filter. Another option is to use a sensor with a color filter array that can distinguish between the second diffracted order of the shortest wavelengths and the first diffracted order of the longest wavelengths. However, construction of filters without edge artifacts or filters which change properties across the dimensions of the filter is typically expensive, and such filters are not generally available as production components.

BRIEF DESCRIPTION OF THE INVENTION

It is an object of the invention to provide imaging spectrometers and cameras that can operate over an extended spectral range. It is a further object of the invention to provide such devices that can effectively sense spectral content across a desired range while being sized to fit in the form factor for a medical scope camera.

According to a first aspect of the invention, an imaging spectrometer includes a prism that refracts incident light in at least a spectral range for spectrographic analysis with a shortest wavelength ($\lambda_S$) and a longest wavelength ($\lambda_L$). A diffraction grating is positioned in optical alignment with the prism and diffracts the incident light. The refraction from the prism and the diffraction from the blazed diffraction grating for a set of diffraction orders used for the spectrographic analysis both increase a deflection angle of the incident light from an original optical axis. One or more sensors are positioned to detect incident light that has passed through the prism and diffraction grating. The spectral range spans greater than an octave such that $\lambda_L>2\lambda_S$. The combined refraction and diffraction of the prism and the blazed diffraction grating are such that a second diffracted order of $\lambda_S$ does not spatially overlap with a first diffracted order of any wavelengths shorter than $\lambda_L$ at the one or more sensors, and there is sufficient diffraction into the second order for wavelengths between $\lambda_S$ and a selected wavelength ($\lambda_C$) in the spectral range such that the second order diffraction for wavelengths between $\lambda_S$ and $\lambda_C$, and the first order diffraction for wavelengths between $\lambda_C$ and $\lambda_L$, are detected with the one or more sensors in different spatial regions to perform the spectrographic analysis for the spectrum from $\lambda_S$ to $\lambda_L$. According to some implementations of the first aspect, a scanning system is included for operating on the incident light such that a second spatial dimension of the image is captured time sequentially as a series of frames.

According to a second aspect of the invention, an imaging spectrometer camera is adapted to receive incident light from a medical scope. The imaging spectrometer camera includes an optical channel receiving and focusing incident light, and an imaging spectrometer positioned downstream from the optical channel. The imaging spectrometer includes a scanning system for adjusting a relative position of the imaging spectrometer with respect to the optical channel. A prism refracts incident light in at least a spectral range for spectrographic analysis with a shortest wavelength ($\lambda_S$) and a longest wavelength ($\lambda_L$). A blazed diffraction grating is positioned in optical alignment with the prism and diffracts the incident light. The refraction from the prism and the diffraction from the blazed diffraction grating for a set of diffraction orders used for the spectrographic analysis both increase a deflection angle of the incident light from an original optical axis. A focal plane array sensor is positioned downstream from the prism and blazed diffraction grating which detects the second order diffraction for wavelengths between $\lambda_S$ and a selected wavelength ($\lambda_C$) in the spectral range and the first order diffraction for wavelengths between $\lambda_C$ and $\lambda_L$ simultaneously along one spatial axis. The spectral range spans greater than an octave such that $\lambda_L>2\lambda_S$. The combined refraction and diffraction of the prism and the blazed diffraction grating are such that a second diffracted order of $\lambda_S$ does not spatially overlap with a first diffracted order of any wavelengths shorter than $\lambda_L$ at the focal plane array sensor.

According to some implementations of the first and second aspects, the diffraction grating is a blazed diffraction grating and has a grating blaze angle with a maximum diffraction efficiency in the first order at a wavelength ($\lambda_P$) such that $0.65<\lambda_P/\lambda_L<0.8$.

According to some implementations of the first and second aspects, the spectral range of the spectrometer is approximately 430-1000 nm. In such implementations, the value of $\lambda_C$ may be approximately 525 nm.

According to some implementations of the first and second aspects, the spectral range of the spectrometer is approximately 500-1100 nm.

According to some implementations of the first and second aspects, the one or more sensors comprise a single focal plane array sensor which detects the second order diffraction for wavelengths between $\lambda_S$ and $\lambda_C$, and the first order diffraction for wavelengths between $\lambda_C$ and $\lambda_L$ simultaneously along one spatial axis. One spatial dimension of an image may be captured along a sensor axis perpendicular to the axis capturing the spectral range.

According to some implementations of the first and second aspects, both the first and second diffractive orders of the wavelengths near $\lambda_C$ are used in calculation of a resultant spectrum.

According to some implementations of the first and second aspects, a spectral filter is included which blocks wavelengths outside of the spectral range of the spectrometer from entering the spectrometer.

These and other features of the invention will be apparent from the following description of the preferred embodiments, considered along with the accompanying drawings.

BRIEF DESCRIPTION OF THE DRAWINGS

The invention is further explained by the following exemplary descriptions of particular embodiments.

DETAILED DESCRIPTION OF THE VARIOUS EMBODIMENTS

Figure 1:
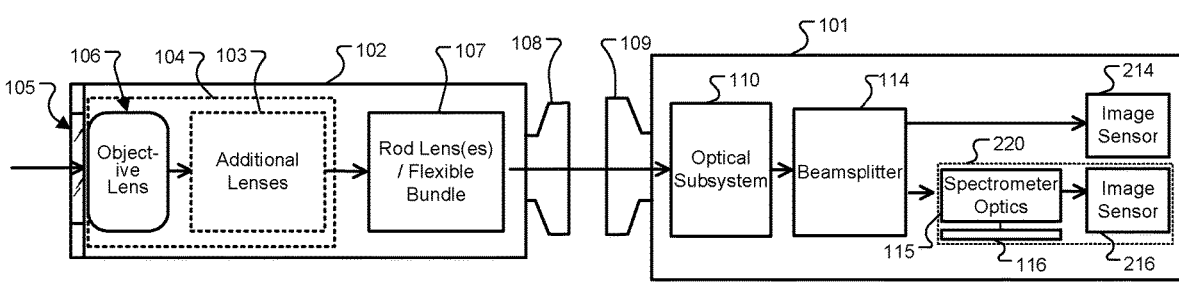
FIG. 1 is a block diagram of an imaging spectroscopy device according to an example embodiment of the invention.

FIG. 1 is a block diagram of an imaging spectroscopy device 100 according to an example embodiment of the invention. Imaging spectroscopy device 100 ("device 100") includes a camera head 101 which may have an endoscope 102 attached via connectors 108 and 109. In some embodiments, an endoscope 102 and camera head 101 may be integrated into a single housing with no connectors needed. In some embodiments, device 100 is provided as only the camera head 101 adapted to be connected to a suitable endoscope or other medical scope. In other embodiments, an imaging spectrometer as described herein may be employed with other imaging arrangements that do not use a scope. Connectors 108 and 109 in this embodiment constitute what is generally called a "claw coupling" or dock-clutch coupling, comprising a clutch that couples two components, whereby at least one or both components are rotatable. Preferably, the claw (109) of the claw coupling is designed such that the eyepiece cup (108) is pushed towards the interface portion to engage the connection. Connectors 108 and 109 may be any suitable connector allowing light to pass from endoscope 102 to camera head 101. Various structural components supporting the depicted elements are omitted in the diagrams herein, as well as other components such as illumination lights sources and controls, which are known in the art and are not shown in order to avoid obscuring the relevant details of the example embodiments of the invention.

Camera head 101 includes an optical subsystem 110 that transmits light used for hyperspectral or multispectral imaging in a desired spectrum, which may include non-visible light wavelengths. Optical subsystem 110 positioned at or behind a central window of connector 109 to receive and condition image light from the endoscope 102. Optical subsystem 110 typically includes a number of lenses for focusing, as further described below. Many suitable lenses and combinations of lenses may be used for optical subsystem 110.

An optional beamsplitter 114 is positioned downstream from the first optical subsystem and separates light into two beams, one directed toward a first image sensor 214 which produces visible light images to accompany the images produced by the other beam using the spectrometer.

An imaging spectrometer 220 receives the imaging light from beamsplitter 114. Imaging spectrometer 220 includes a spectrometer optical assembly 115, a scanning mechanism 116, and an image sensor 216. In some embodiments, more than one image sensor may be used, however a single image sensor is preferred. Spectrometer optical assembly 115 is optically positioned downstream from the beamsplitter and includes various elements for collimating, refracting, and diffracting the image light, as well as elements of a scanning system. For embodiments without a beamsplitter, spectrometer optical assembly 115 is directly downstream from optical subsystem 110, and image sensor 214 may not be present. In this embodiment, scanning mechanism 116 is mechanically coupled to at least a portion of the spectrometer optics for achieving mechanical movement needed to perform scanning operations. Scanning mechanism 116 may be a push broom scanning mechanism operating in cooperation with a slit in the spectrometer optical assembly, or another suitable scanning mechanism which may move or rotate one or more optical elements to perform a line-by-line scanning operation for the spectrometer, as further described below.

In some embodiments, device 100 includes an endoscope 102 as depicted at the left of the block diagram. The depicted endoscope is an example only, and many endoscope designs are suitable, including rigid and flexible endoscopes. Endoscope 102 includes a cover glass 105 at its distal tip, which in this version faces directly along the longitudinal axis of the endoscope 102, but may also be positioned at an angle relative to the longitudinal axis as is known in the art. Behind, or on the proximal side of, cover glass 105 is shown a preferred position for the objective lens 106, set against or very near cover glass 105 and preferably assembled together with the cover glass in construction. Objective lens 106 may be part of an objective lens group 104 which may include one or more additional lenses 103. The particular number and arrangement of lenses in the endoscope 102 will vary widely depending on the application. Optically arranged or attached at the proximal side of objective lens 106 or objective lens group 104 is flexible fiber bundle or a series of one or more rod lenses 107, which serve to pass the light down endoscope 102 in the proximal direction. For embodiments with a flexible shaft, the flexible fiber bundle is used. For rigid or semi-rigid shafts, one or several rod lenses 107 are employed, which may be separated by spacers or other lenses in any suitable manner known in the art.

Figure 2:
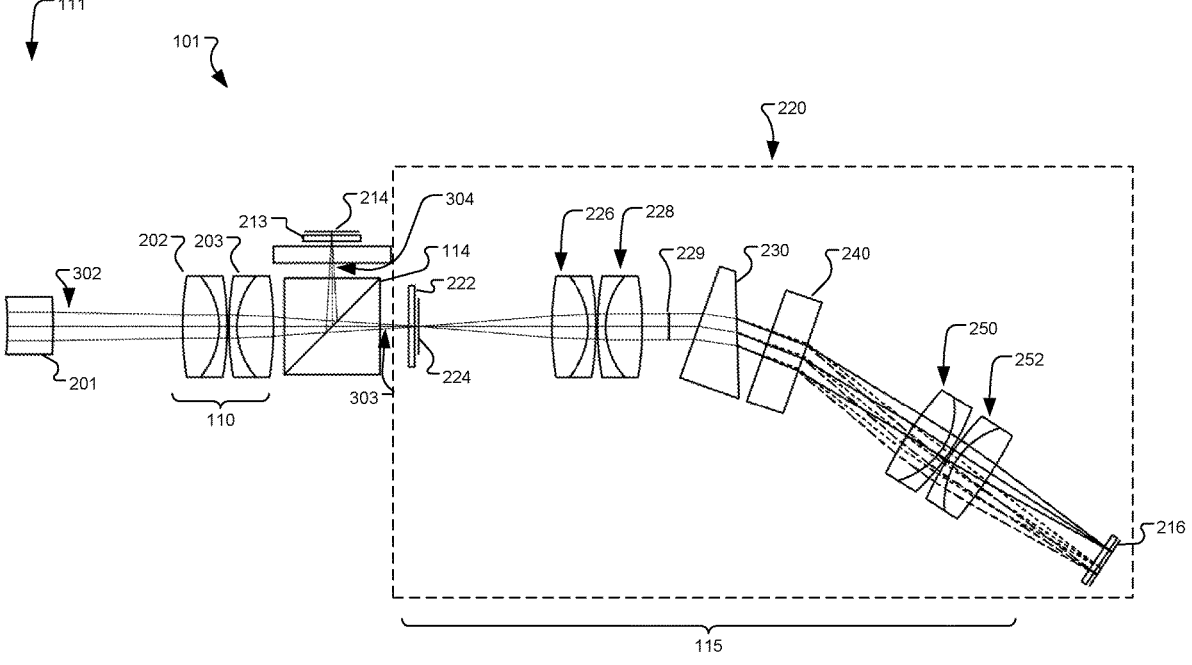
FIG. 2 is a partial cross section diagram of a camera head showing the optical assembly construction according to an example embodiment.

FIG. 2 is a partial cross section diagram of a camera head 101 showing the optical assembly construction according to an example embodiment. The cross section includes a light ray diagram showing image light 302 passing through the assembly, and then being directed by a beamsplitter 114 toward image sensors 214 for white light imaging, and image sensor 216 in spectrometer 220 for image spectroscopy. The depicted optical elements are in diagram form only and are not drawn to scale. The depicted optical assembly may be employed with devices and systems having an integrated camera or an external detachable camera head.

As shown, image light 302 enters the optical assembly at a cover glass 201 in this embodiment. Image light 302 then passes downstream to optical subsystem 110, which in this embodiment includes doublet lens 202 and a doublet lens 203. Doublet lens 202 includes a bi-convex lens followed by a concave-convex lens, which together have a slightly positive power. Doublet lens 203 includes a convex-concave lens followed by a bi-convex lens, the lens pair together has a positive power and serve to focus image light 302. These two lens pairs are designed to focus and align image light 302 along the central optical axis toward beamsplitter 114 while optionally mitigating chromatic aberrations. Various other lens combinations may be used to achieve the same result in various embodiments.

In this embodiment, beamsplitter 114 is constructed of two prisms, with a suitable beamsplitting layer formed of a partially reflective coating along their adjacent surface, by which the image light is split with a first portion passing through along first optical path illustrated by image light 303 and a second portion reflected upward along second optical path illustrated by imaging light 304. In this embodiment, the partially reflective coating reflects image light of the visible spectrum, preferably reflecting as little of the light necessary for white light imaging in order to preserve a majority of the image light intensity in the visible range and all of the light in the non-visible spectra for spectrographic analysis. First image sensor 214 is positioned downstream of a cover glass or protective layer 213, with the image sensor oriented perpendicularly the longitudinal axis of camera head 101.

Imaging spectrometer 220 is positioned downstream of beamsplitter 114 to receive incident light 303 from beamsplitter 114. Imaging spectrometer 220 generally includes spectrometer optical assembly 115 and second image sensor 216, and a scanning mechanism (116, FIG. 1). In this embodiment, spectrometer optical assembly 115 includes an optional filter 222 used to filter incident light to remove wavelengths outside of a desired spectral range for spectrographic analysis. Generally, the spectral range has a shortest wavelength ($\lambda_S$) and a longest wavelength ($\lambda_L$), which vary in different embodiments depending on the application.

Optically positioned downstream of optional filter 222 is a slit 224, positioned at the focal point created by optical subsystem 110 and oriented perpendicularly to the optical axis of incident light 303 such that with respect to the drawing the slit extends into the page to provide a horizontal slit across the incident light. Optically positioned downstream of slit 224 is a collimating lens group including a doublet lens 226 and a doublet lens 228, which each include a convex-convex lens and a concave-convex lens selected to collimate the diverging incident light while optionally minimizing chromatic aberrations across the spectral range. Various other collimating lens arrangements may be used to achieve the same function in various embodiments.

Figure 3:
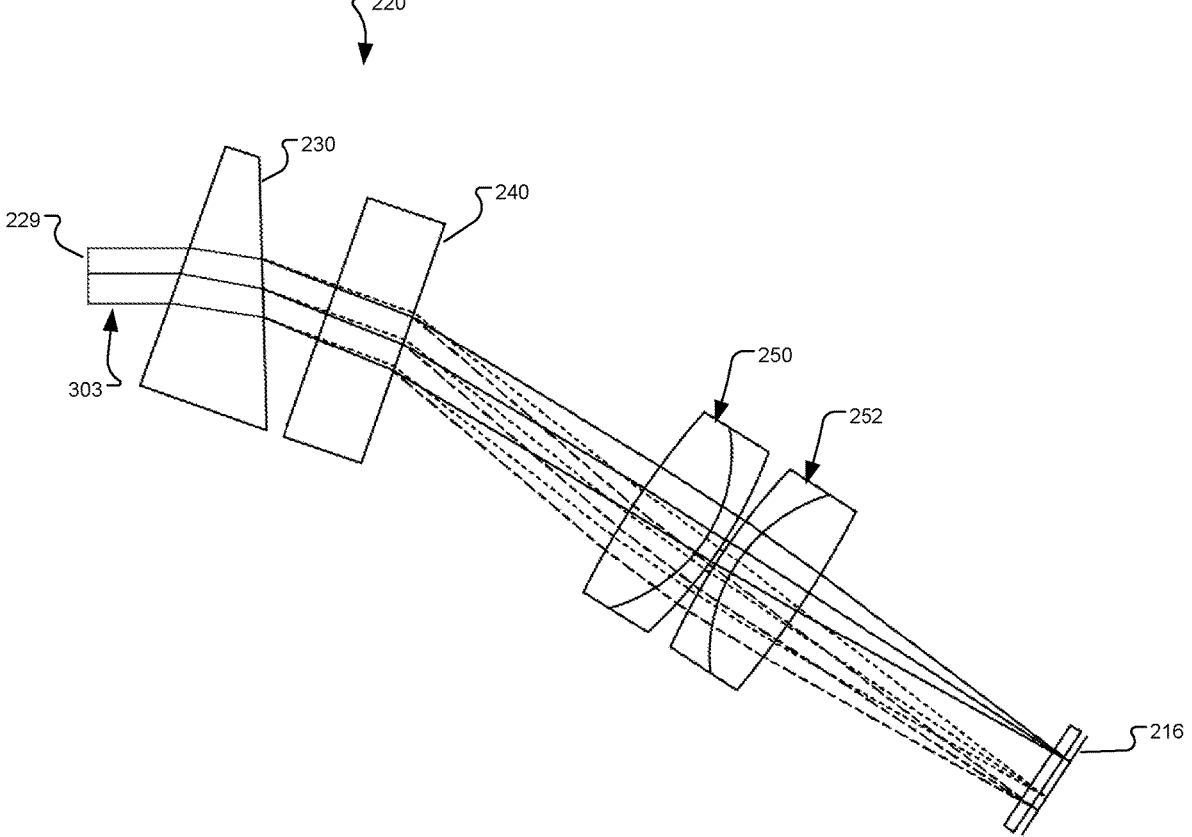
FIG. 3 shows an enlarged view of a portion of the imaging spectrometer of FIG. 2.

FIG. 3 shows an enlarged view of a portion of the imaging spectrometer 220 of FIG. 2. Referring to FIG. 2 and FIG. 3, optically positioned downstream of the collimating lens group is a prism 230 that refracts the collimated incident light in at least a spectral range for spectrographic analysis. A stop 229 may be used to block light outside of a designated region from entering prism 230. Prism 230 refracts the incident light at an angle, depicted downward in the drawing, from the optical axis of the incoming incident light. A blazed diffraction grating 240 is positioned in optical alignment with prism 230 to receive the refracted incident light. As depicted, diffraction grating 240 is oriented at an angle to the original optical axis of optical assembly 115. Diffraction grating 240 diffracts the incident light and is oriented such that the refraction from prism 230 and the diffraction from diffraction grating 240 both increase a deflection angle of the incident light from an original optical axis for a set of diffraction orders used for the spectrographic analysis. In this embodiment, the set of diffraction orders used is the first and second diffraction orders, as further described below.

The diffracted incident light from diffraction grating 240 is focused toward image sensor 216 by a pair of doublet lenses 250 and 252. Various lenses and lens combinations may be employed in different embodiments to perform the focusing functions. In this embodiment, lens doublet 250 includes a bi-convex lens and a concave-convex lens. Lens doublet 252 also includes a convex-concave lens and a bi-convex lens. In some embodiments, such as that shown in FIGS. 2 and 3, doublet lenses 250 and 252 are the same convex-convex and menisci as lenses 226 and 228 (FIG. 2).

Image sensor 216 is positioned downstream from doublet lenses 250 and 252 to detect incident light that has passed through the prism and diffraction grating. In this embodiment, Image sensor 216 is a single focal plane array sensor which detects the second order diffraction for wavelengths between $\lambda_S$ and $\lambda_C$, and the first order diffraction for wavelengths between $\lambda_C$ and $\lambda_L$ simultaneously along one spatial axis Because of the refraction and diffraction, various spectral portions of the incident light are distributed along one axis of image sensor 216, which is positioned to detect these portions, which include selected first and second diffraction orders from diffraction grating 240. The spectral range for which imaging spectroscopy is performed spans greater than an octave such that $\lambda_L > 2\lambda_S$. The combined refraction and diffraction of prism 230 and diffraction grating 240 are such that a second diffracted order of $\lambda_S$ does not spatially overlap with a first diffracted order of any wavelengths shorter than $\lambda_L$ at the one or more sensor. As further described below with respect to FIG. 5 and FIG. 6, there is sufficient diffraction into the second order for wavelengths between $\lambda_S$ and a selected wavelength ($\lambda_C$) in the spectral range such that the second order diffraction for wavelengths between $\lambda_S$ and $\lambda_C$, and the first order diffraction for wavelengths between $\lambda_C$ and $\lambda_L$, are detected with the one or more sensors in different spatial regions to perform the spectrographic analysis for the spectrum from $\lambda_S$ to $\lambda_L$.

In this embodiment, imaging spectrograph 220 is held in a modular assembly which is moved by scanning mechanism 116 (FIG. 1) to perform the scanning function. The movement is in the up-down direction with respect to the drawing in a push-broom fashion, such that slit 224 is moved to a different location within incident light 303 to acquire a new line of imaging spectrometer data. Multiple lines are acquired in this fashion to produce an imaging spectrometer image.

Figure 4:
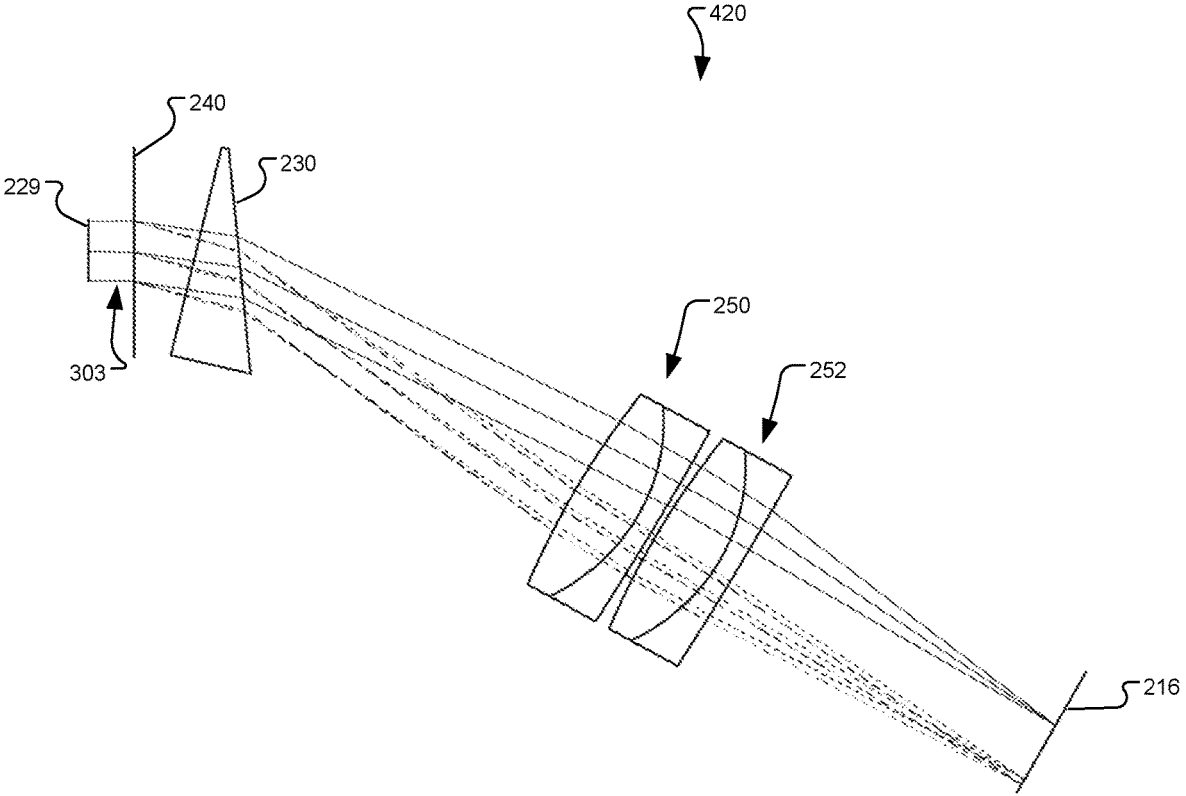
FIG. 4 shows an enlarged view of a portion of an imaging spectrometer according to another embodiment.

FIG. 4 shows an enlarged view of a portion of an imaging spectrometer 420 according to another embodiment. The depicted embodiment is suitable for use in imaging spectrometer 220 of FIG. 2, and for use in implementing an imaging spectrometer according to other embodiments. As shown, prism 230 is optically arranged following diffraction grating 240 in this embodiment, rather than the diffraction grating following the prism. prism 230 is positioned in optical alignment with blazed diffraction grating 240 to receive the refracted incident light. As depicted, prism 230 is oriented at an angle to the original optical axis of optical assembly 115. Prism 230 refracts the incident light and is oriented such that the diffraction from diffraction grating 240 and the refraction from prism 230 both increase a deflection angle of the incident light from an original optical axis for a set of diffraction orders used for the spectrographic analysis. The properties described with respect to FIG. 2 and FIG. 3 are also present in this embodiment, that is the spectral range for which imaging spectroscopy is performed spans greater than an octave such that $\lambda_L > 2\lambda_S$, and the combined refraction and diffraction of prism 230 and diffraction grating 240 are such that a second diffracted order of $\lambda_S$ does not spatially overlap with a first diffracted order of any wavelengths shorter than $\lambda_L$ at the one or more sensor.

Figure 5:
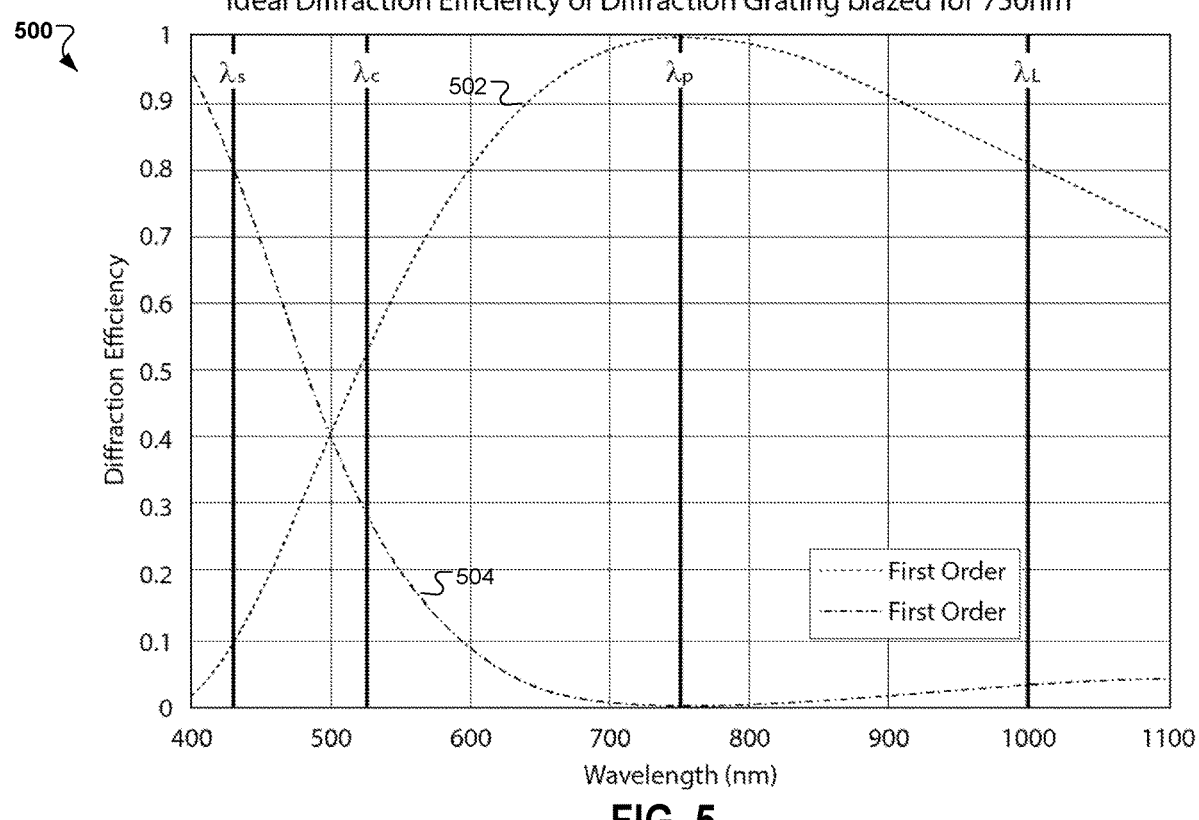
FIG. 5 shows a chart illustrating properties of a diffraction grating according to some embodiments.

FIG. 5 shows a chart 500 illustrating properties of a diffraction grating according to some embodiments. The vertical axis shows diffraction efficiency, and the horizontal axis shows light wavelength in nanometers (nm). Graph 502 shows the first order diffraction efficiency of a diffraction grating, such as diffraction grating 240 of FIG. 2, while graph 504 shows the second order diffraction efficiency. In this version, the spectral range of the spectrometer is approximately 430-1000 nm, as shown by $\lambda_S$ and $\lambda_L$ on chart 500. By "approximately", as used herein, it is meant that the particular values may vary slightly from the claimed values, such as a variation of up to 5%. The diffraction grating has a grating blaze angle with a maximum diffraction efficiency at 750 nm for the first order, as shown at the wavelength labeled $\lambda_P$.

A selected cutoff wavelength $\lambda_C$ is shown, below which the imaging spectrometer as described herein uses the second order diffractions to detect spectral content, rather than the first order diffractions. In this embodiment, $\lambda_C$ is approximately 525 nm. In other embodiments, a different value $\lambda_C$ may be used, depending mainly on the total spectrum desired to be analyzed, that is the values of $\lambda_S$ and $\lambda_L$. For example, in another embodiment the spectral range of the spectrometer is approximately 500-1100 nm, and a higher value of $\lambda_C$ is used. $\lambda_S$ can be seen in the chart of FIG. 5, at and near the wavelength $\lambda_C$, both the first and second diffractive orders will have relatively low intensity or power at the sensor due to the diffraction efficiency. $\lambda_S$ such, in some embodiments, both the first and second diffraction orders for the wavelengths near $\lambda_C$ may be used in the calculation of the spectral content, as further described below. By "near", it is meant that the adjacent spectral bands on either side which have such low intensity may be calculated with such a technique.

In this embodiment, the blazed diffraction grating has a grating blaze angle with a maximum diffraction efficiency in the first order at a wavelength $\lambda_P$ of 750 nm, which is 0.75 times the long end wavelength of $\lambda_L$. Generally, the present inventor has discovered that the combination of spatial dispersion of the spectrum from diffraction and refraction is able to achieve the desired efficiency characteristics as shown in FIG. 5 along with the spatial distribution discussed below with respect to FIG. 6 when the diffraction grating is selected such that $0.65 < \lambda_P / \lambda_L < 0.8$. Embodiments which use such characteristics of the diffraction grating provide advantages in allowing a large spectral range to be detected without spatial overlap of the first and second diffraction orders, while still providing enough power in each spectral band for fast and efficient detection using a single sensor.

This combination also allows for reducing components such as filters that are often optically arranged in front of a sensor to block overlapping second order diffractions. Thus, the overall size of the spectrometer optics can be reduced while still allowing imaging spectroscopy to be performed on a relatively large frequency range, greater than an octave. Additionally, the cost of such a spectrographic system is likely reduced over a conventional system.

Figure 6:
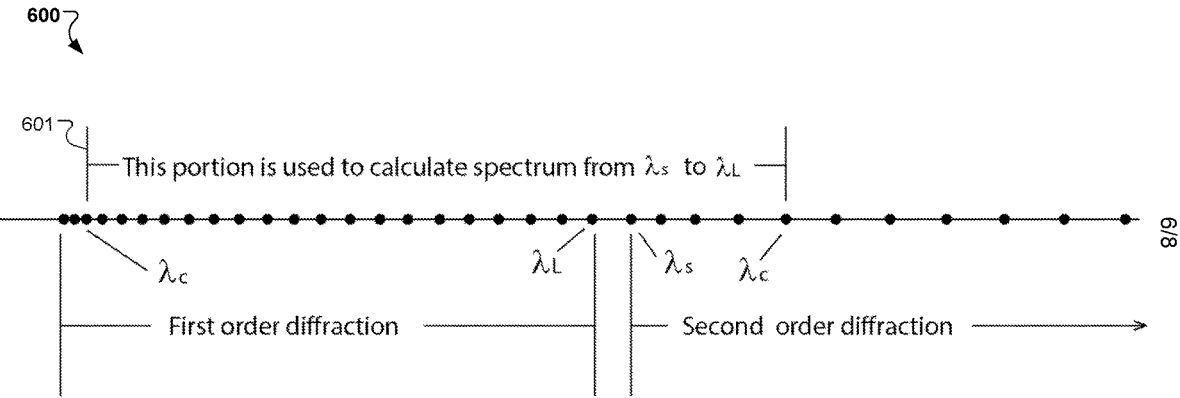
FIG. 6 shows a diagram illustrating the spatial distribution of first and second order diffractions in a sensor plane according to some embodiments.

FIG. 6 shows a diagram 600 illustrating the spatial distribution of first and second order diffractions in a sensor plane according to some embodiments. The horizontal axis shows position along the direction of diffraction at the sensor plane. The shaped dots represent the spatial location of the individual wavelengths identified by the dots on graphs 502 and 504 of FIG. 5. Labeled on the diagram is a region 601 to be captured by the sensor which extends from the first order diffraction of $\lambda_C$ to the second order diffraction of $\lambda_C$. Region 601 is used to detect and calculate the continuous spectrum from $\lambda_S$ to $\lambda_L$. The first order diffraction for wavelengths shorter than $\lambda_C$ and the second order diffraction for wavelengths longer than $\lambda_C$ are preferably not used. Typically, light from these unused regions will fall outside the active area of the sensor and not be collected. Preferably, the prism and diffraction grating are designed to place the spatial position of the $\lambda_S$ second order diffraction slightly separated from the first order diffraction of $\lambda_L$.

In some embodiments, both the first and second diffractive orders of the wavelengths near $\lambda_C$ are detected and combined in the calculation of the resultant spectral analysis. By "near" it is meant that at $\lambda_C$, and possibly one or two quantized spectral bands around $\lambda_C$, both diffractive orders may be used. Exactly how large the frequency range is for which both diffractive orders are used may vary depending on how the frequencies are quantized, and how the sensor is spatially positioned with respect to the diffracted light, as illustrated in FIG. 6. For example, as seen on the chart of FIG. 5, the dots every 25 nm on graphs 502 and 504 represent quantized levels for which spectral content is calculated. Due to the properties of the prism and diffraction grating, the spatial spread between quantization levels increases toward the longer end of each diffraction order. This is only an example, and preferably higher spectral resolutions are used when possible. As an example, if a sensor with 1080 lines along the relevant axis is used, in each line measures a smaller portion of the spectrum as the spatial diffraction grows as shown in FIG. 6. Therefore, to quantize the spectrum by wavelength spanning $\lambda_S$ to $\lambda_L$, an increasing number of sensor lines are used for each quantization level. $\lambda_S$ can be seen on FIG. 6, the first order diffraction at a quantized level of $\lambda_C$ will be detected using fewer sensor lines (for example one or two) than the first order diffraction at $\lambda_L$ and the second order diffractions. This example is intended to illustrate how portions of both diffraction orders may be detected, and the particular method used to calculate, quantize, and display the spectrum may vary in different embodiments.

Figure 7:
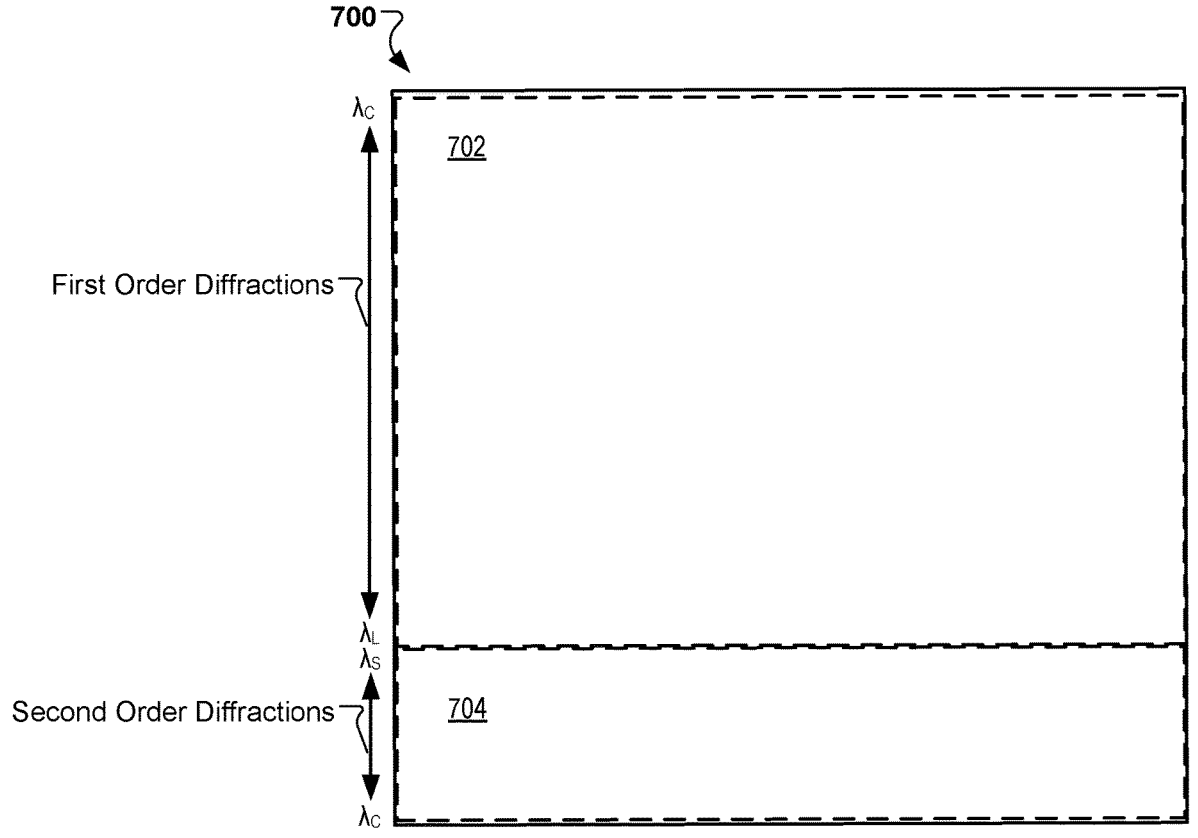
FIG. 7 shows a diagram illustrating the position of diffractions along an image sensor according to some embodiments.

FIG. 7 shows a diagram illustrating the position of diffractions along an image sensor 700 according to some embodiments. The left-to-right dimension illustrated in FIG. 6 is oriented top-to-bottom on image sensor 700. In this embodiment, sensor 700 is a single focal plane array sensor which detects the first order diffraction for wavelengths between $\lambda_C$ and $\lambda_L$ along the vertical spatial axis in region 702, and simultaneously detects the second order diffraction for wavelengths between $\lambda_S$ and $\lambda_C$, along the vertical spatial axis in sensor region 704. The horizontal dimension of image sensor 700 captures a horizontal line or band of the incoming light in a single frame. The band is updated to scan "line by line" with reference to the field of incoming light, along which a slit or other selective blocking structure is moved incrementally using a scanning system such as slit 224 and scanning mechanism 116. The scanning system operates on the incident light such that a second spatial dimension of the image spectroscopy image is captured time sequentially as a series of frames. Various other scanning systems may be used in various embodiments to achieve the same result.

Figure 8:
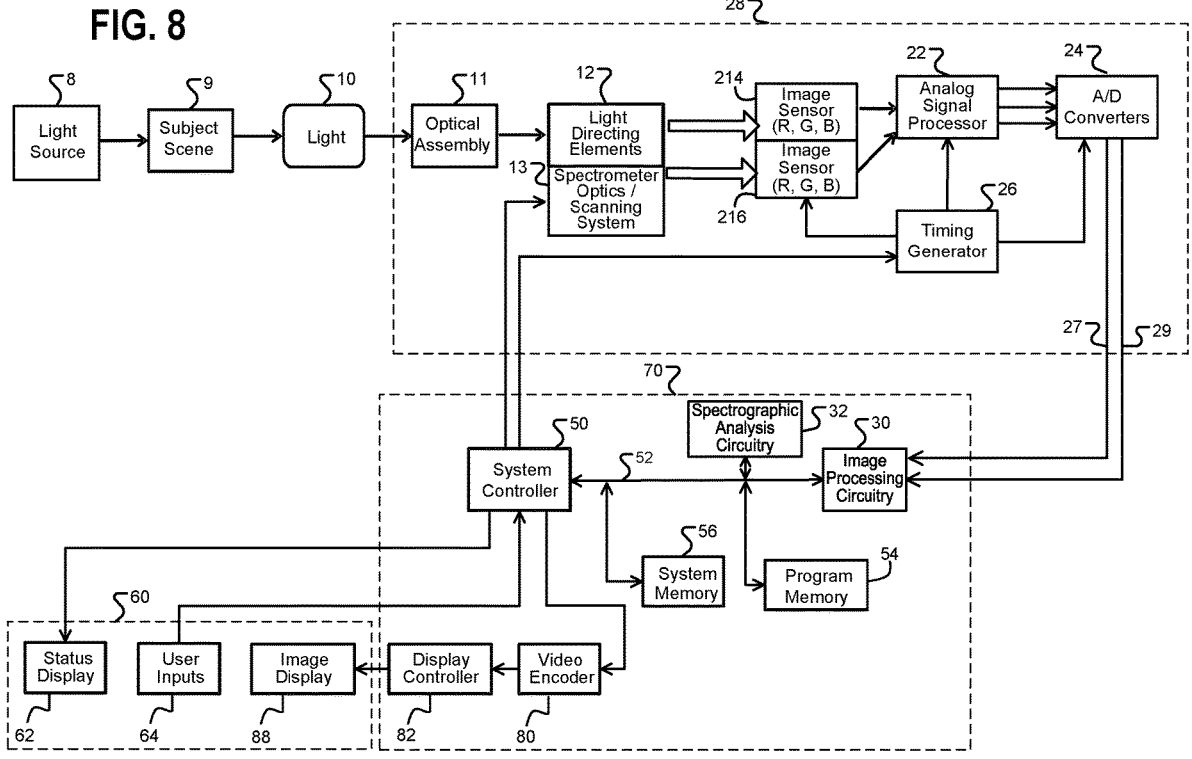
FIG. 8 is a hardware block diagram of system including an example image capture device according to an example embodiment of the invention.

FIG. 8 is a block diagram of an optical instrument system according to an example embodiment of the present invention. The depicted design is suitable for implementing the various embodiments described above, as well as other embodiments. While this example circuit is shown for an endoscope, the present invention is applicable to other instruments such as borescopes, or exoscopes, for example, as well as other scopes and imaging systems in which imaging spectrometry is useful, especially in a compact form.

A light source 8 illuminates subject scene 9 and light 10 reflected from (or, alternatively, as in the case of certain fluorescence imaging applications, transmitted or emitted by) the subject scene forms an optical image via an optical channel assembly 11, where the light is passed to the camera head, typically using a relay system comprising rod lenses. At the camera head the light is focused, aligned with the scope axis or a desired optical axis, and passed to a proximal side of optical channel assembly 11 where light directing elements 12, such as beamsplitter 114 described above, direct different portions of the light to form an image on first solid-state image sensors 214 and direct light through spectrometer optics and scanning system 13 to second solid-state image sensor 216. While two image sensors are shown in this implementation, single-sensor designs may be implemented by removing the first image sensor 214. In single sensor implementations, no white light image is captured.

In this embodiment, optical channel assembly 11 includes an imaging system and may be constructed according to a variety of known methods. Image sensors 214 and 216 convert the incident light to an electrical signal by, for example, integrating charge for each picture element (pixel). The image sensors 214 and 216 may be active-pixel type complementary metal oxide semiconductor sensors (CMOS APS) or a charge-coupled device (CCD), to give just two possible examples. The output analog signal from the image sensors is processed by analog signal processor 22 and applied to analog-to-digital (A/D) converter 24 for digitizing the analog sensor signals. In some versions (typically CMOS designs), the analog signal processing and A/D converters may be integrated into individual sensor modules attached to each sensor 214 and 216.

The system's camera 28 generally includes timing generator 26, which produces various clocking signals to select rows and pixels and synchronizes the operation of image sensors 214 and 216, analog signal processor 22, and A/D converter 24. The scanning mechanism of the scanning system may be controlled by system controller 50 or by a local timing mechanism in camera 28. A camera head electronic assembly typically houses image sensors 214 and 216, while the locations of each of analog signal processor 22, the A/D converter 24, and the timing generator 26 may vary, for example in the scope handle 102. The non-optical, functional elements of the camera 28 may be fabricated as a single integrated circuit as is commonly done with CMOS image sensors or they may be separately-fabricated integrated circuits.

The system controller 50 controls the overall operation of the image capture device based on a software program stored in program memory 54. This memory can also be used to store user setting selections and other data to be preserved when the camera 28 is turned off. Data connections 27 and 29 carry the digital image data of image sensors 214 and 216 to image processing circuitry 30, which may be integrated with system controller 50 in some versions or may be a separate programmable logic device or data processor. A data bus 52 provides a pathway for address, data, and control signals and spectrographic analysis data from spectrographic analysis circuitry 32. Control signals are sent to spectrometer optics/scanning system 13 and timing generator 26. In some variations, data bus 52 may also carry data connections 27 and 29.

Image processing circuitry 30 performs image processing operations including the operations to form images from image sensor 214 and partial spectrograph images from image sensor 216, that is the individual frames which are combined for spectrographic analysis. Spectrographic analysis circuitry 32 receives the partial spectrograph images and performs spectrographic analysis including normalizing the data based on the spectral transfer function of the spectrometer optics, calculating spectral content, and creating a combined image spectral data set including spectral data for each image pixel acquired based across a complete line-by-line scan by the scanning system. Spectrographic analysis circuitry 32 may also perform spectral analysis to identify, classify, or highlight features found in the image spectral data set, and prepare representative images for display to visualize or otherwise present the spectrographic data in the spectral data set. As such, spectrographic analysis circuitry 32 may perform any suitable processing and visualization techniques employed with multispectral imaging (MSI) and hyperspectral imaging (HSI) analysis.

Processed image data are continuously sent to video encoder 80 to produce a video signal. This signal is processed by display controller 82 and presented on image display 88. This display is typically an HD, UHD, or 4K format liquid crystal display backlit with light-emitting diodes (LED LCD), although other types of displays may be used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 may manage the graphical user interface (GUI) presented on one or more of the displays (e.g., on image display 88). The GUI typically includes menus for making various option selections.

Image processing circuitry 30, spectrographic analysis circuitry 32, system controller 50, system and program memories 56 and 54, video encoder 80, and display controller 82 may be housed within camera control unit (CCU) 70. CCU 70 may be responsible for powering and controlling light source 8 and/or camera 28. As used herein "CCU" refers to units or modules that power, receive data from, manipulate data from, transmit data to, and/or forwards data from optical instrument cameras. CCU functionalities may be spread over multiple units known as, for example, a "connect module", "link module", or "head module".

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. An imaging spectrometer comprising:
a prism that refracts incident light in at least a spectral range for spectrographic analysis with a shortest wavelength ($\lambda_S$) and a longest wavelength ($\lambda_L$);
a diffraction grating, positioned in optical alignment with the prism, that diffracts the incident light, wherein the refraction from the prism and the diffraction from the diffraction grating for a set of diffraction orders used for the spectrographic analysis both increase a deflection angle of the incident light from an original optical axis; and
one or more sensors positioned to detect incident light that has passed through the prism and diffraction grating, wherein the spectral range spans greater than an octave such that $\lambda_L > 2\lambda_S$, and wherein the combined refraction and diffraction of the prism and the diffraction grating are such that a second diffracted order of $\lambda_S$ does not

12 spatially overlap with a first diffracted order of any wavelengths shorter than $\lambda_L$ at the one or more sensors, and there is sufficient diffraction into the second order for wavelengths between $\lambda_S$ and a selected wavelength ($\lambda_C$) in the spectral range such that the second order diffraction for wavelengths between $\lambda_S$ and $\lambda_C$, and the first order diffraction for wavelengths between $\lambda_C$ and $\lambda_L$, are detected with the one or more sensors in different spatial regions to perform the spectrographic analysis for the spectrum from $\lambda_S$ to $\lambda_L$.

2. The imaging spectrometer according to claim 1 wherein the diffraction grating is a blazed diffraction grating and has a grating blaze angle with a maximum diffraction efficiency in the first order at a wavelength ($\lambda_P$) such that $0.65 < \lambda_P/\lambda_L < 0.8$.

3. The imaging spectrometer according to claim 1 wherein the spectral range of the spectrometer is approximately 430-1000 nm.

4. The imaging spectrometer according to claim 3 wherein $\lambda_C$ is approximately 525 nm.

5. The imaging spectrometer according to claim 1 wherein the spectral range of the spectrometer is approximately 500-1100 nm.

6. The imaging spectrometer according to claim 1 wherein the one or more sensors comprise a single focal plane array sensor which detects the second order diffraction for wavelengths between $\lambda_S$ and $\lambda_C$, and the first order diffraction for wavelengths between $\lambda_C$ and $\lambda_L$ simultaneously along one spatial axis.

7. The imaging spectrometer according to claim 6 wherein one spatial dimension of an image is captured along a sensor axis perpendicular to the axis capturing the spectral range.

8. The imaging spectrometer according to claim 7 further comprising a scanning system operating on the incident light such that a second spatial dimension of the image is captured time sequentially as a series of frames.

9. The imaging spectrometer according to claim 1 wherein both the first and second diffractive orders of the wavelengths near $\lambda_C$ are used in calculation of a resultant spectrum.

10. The imaging spectrometer according to claim 1 further comprising a spectral filter which blocks wavelengths outside of the spectral range of the spectrometer from entering the spectrometer.

11. An imaging spectrometer camera adapted to receive incident light from a medical scope, comprising:
an optical channel receiving and focusing incident light; and
an imaging spectrometer positioned downstream from the optical channel and comprising:
a scanning system for adjusting a relative position of the imaging spectrometer with respect to the optical channel;
a prism that refracts incident light in at least a spectral range for spectrographic analysis with a shortest wavelength ($\lambda_S$) and a longest wavelength ($\lambda_L$);
a diffraction grating, positioned in optical alignment with the prism, that diffracts the incident light, wherein the refraction from the prism and the diffraction from the diffraction grating for a set of diffraction orders used for the spectrographic analysis both increase a deflection angle of the incident light from an original optical axis; and
a focal plane array sensor positioned downstream from the prism and diffraction grating which detects the second order diffraction for wavelengths between $\lambda_S$ and a selected wavelength ($\lambda_C$) in the spectral range

US 12,571,679 B2

13 and the first order diffraction for wavelengths between $\lambda_C$ and $\lambda_L$ simultaneously along one spatial axis, wherein the spectral range spans greater than an octave such that $\lambda_L > 2\lambda_S$, and wherein the combined refraction and diffraction of the prism and the diffraction grating are such that a second diffracted order of $\lambda_S$ does not spatially overlap with a first diffracted order of any wavelengths shorter than $\lambda_L$ at the focal plane array sensor.

12. The imaging spectrometer camera according to claim 11 wherein the diffraction grating is a blazed diffraction grating that has a grating blaze angle with a maximum diffraction efficiency in the first order at a wavelength ($\lambda_P$) such that $0.65 < \lambda_P/\lambda_L < 0.8$.

13. The imaging spectrometer camera according to claim 11 wherein the spectral range of the spectrometer is approximately 430-1000 nm.

14. The imaging spectrometer camera according to claim 13 wherein $\lambda_C$ is approximately 525 nm.

14

15. The imaging spectrometer according to claim 11 wherein the spectral range of the spectrometer is approximately 500-1100 nm.

16. The imaging spectrometer camera according to claim 11 wherein one spatial dimension of an image is captured along a sensor axis perpendicular to the axis capturing the spectral range.

17. The imaging spectrometer camera according to claim 16 wherein the scanning system operates such that a second spatial dimension of the image is captured time sequentially as a series of frames.

18. The imaging spectrometer according to claim 11 wherein both the first and second diffractive orders of the wavelengths near $\lambda_C$ are used in calculation of a resultant spectrum.

19. The imaging spectrometer according to claim 11 further comprising a spectral filter which blocks wavelengths outside of the spectral range of the spectrometer from entering the spectrometer.

20. The imaging spectrometer of claim 11, wherein the diffraction grating is positioned downstream from the prism.

* * * * *